United States Patent
Taylor et al.

(10) Patent No.: US 7,833,168 B2
(45) Date of Patent: Nov. 16, 2010

(54) TARGETED BIOPSY DELIVERY SYSTEM

(75) Inventors: James D. Taylor, Bridgeton, MO (US);
Bruce Olson, Clayton, MO (US);
Stephen Lewis, Florissant, MO (US)

(73) Assignee: Envisioneering Medical Technologies, LLC, St. Louis, MO (US)

( * ) Notice: Subject to any disclaimer, the term of this patent is extended or adjusted under 35 U.S.C. 154(b) by 0 days.

(21) Appl. No.: 11/895,228

(22) Filed: Aug. 23, 2007

(65) Prior Publication Data

US 2007/0293787 A1 Dec. 20, 2007

Related U.S. Application Data

(63) Continuation of application No. 10/842,652, filed on May 10, 2004, now abandoned.

(60) Provisional application No. 60/494,910, filed on Aug. 13, 2003.

(51) Int. Cl.
*A61B 10/00* (2006.01)
*A61B 8/00* (2006.01)
*A61B 8/14* (2006.01)
*A61B 17/34* (2006.01)

(52) U.S. Cl. ................. 600/567; 600/562; 600/564; 600/437; 600/443; 600/461

(58) Field of Classification Search ............. 600/562, 600/564, 567, 101, 102, 109, 117, 139, 146, 600/152, 160, 437, 461, 443, 407
See application file for complete search history.

(56) References Cited

U.S. PATENT DOCUMENTS

| | | | |
|---|---|---|---|
| 5,149,598 A | 9/1992 | Sunshine | |
| 5,398,690 A | 3/1995 | Batten et al. | |
| 5,456,258 A | 10/1995 | Kondo et al. | |
| 5,660,185 A | 8/1997 | Shmulewitz et al. | |
| 5,873,828 A | 2/1999 | Fujio et al. | |
| 6,102,867 A | 8/2000 | Dieta et al. | |
| 6,171,249 B1 | 1/2001 | Chin | |
| 6,179,249 B1 | 1/2001 | Canadas | |
| 6,238,336 B1 | 5/2001 | Ouchi | |
| 6,261,234 B1 | 7/2001 | Lin | |
| 6,261,243 B1 | 7/2001 | Burney | |
| 6,390,973 B1 | 5/2002 | Ouchi | |
| 6,409,666 B1 | 6/2002 | Ito | |

(Continued)

OTHER PUBLICATIONS

U.S. Appl. No. 60/493,406, filed Aug. 7, 2003, Fichtinger et al.

(Continued)

*Primary Examiner*—Max Hindenburg
*Assistant Examiner*—Jeffrey G Hoekstra
(74) *Attorney, Agent, or Firm*—Gordon & Jacobson, PC

(57) ABSTRACT

This invention relates generally to the targeting and biopsy of tissue for medical purposes, and more particularly to a targeted biopsy system which allows planning of tissue to be sampled, targeting of specific areas of tissue in reference to the plan, capturing the tissue sample and recording the source location of the tissue sample, particularly for use in collecting tissue samples from the prostate gland. A further purpose of this invention is to provide a targeted treatment system which allows planning of tissue to be treated, targeting of specific areas of tissue in reference to the plan, and delivering the treatment to the targeted tissue.

31 Claims, 11 Drawing Sheets

U.S. PATENT DOCUMENTS

| | | |
|---|---|---|
| 6,447,477 B2 | 9/2002 | Burney et al. |
| 6,485,411 B1 | 11/2002 | Konstorum et al. |
| 6,685,648 B2 | 2/2004 | Flaherty et al. |
| 6,689,067 B2 | 2/2004 | Sauer et al. |
| 6,884,219 B1 | 4/2005 | Pruter |
| 7,171,255 B2 | 1/2007 | Holupka et al. |
| 2002/0002349 A1 | 1/2002 | Flaherty et al. |
| 2002/0111634 A1 | 8/2002 | Stoianovici et al. |
| 2003/0078502 A1 | 4/2003 | Miyaki et al. |
| 2003/0120154 A1 | 6/2003 | Sauer et al. |
| 2003/0135119 A1 | 7/2003 | Lee et al. |
| 2004/0030250 A1 | 2/2004 | Stewart |
| 2004/0133111 A1 | 7/2004 | Szczech et al. |
| 2005/0203413 A1 | 9/2005 | Fichtinger et al. |

OTHER PUBLICATIONS

"Execution of Robot-Assisted Biopsies Within The Clinical Context," Rovetta et al, Journal of Image Guided Surgery, 1: 280-287, 1995.

"Transrectal Prostate Biopsy Inside Closed MRI Scanner with Remote Actuation, under Real-Time Image Guidance," Fichtinger et al, MICCAAI 2002, LNCS 2488 pp. 91-98, 2002.

"A Robotic System for Transrectal Needle Insertion into the Prostate with Integrated Ultrasound", Chad M. Schneider et al., Proceedings of the 2004 IEEE International conference on Robotics & Automation, Apr. 2004, pp. 365-370.

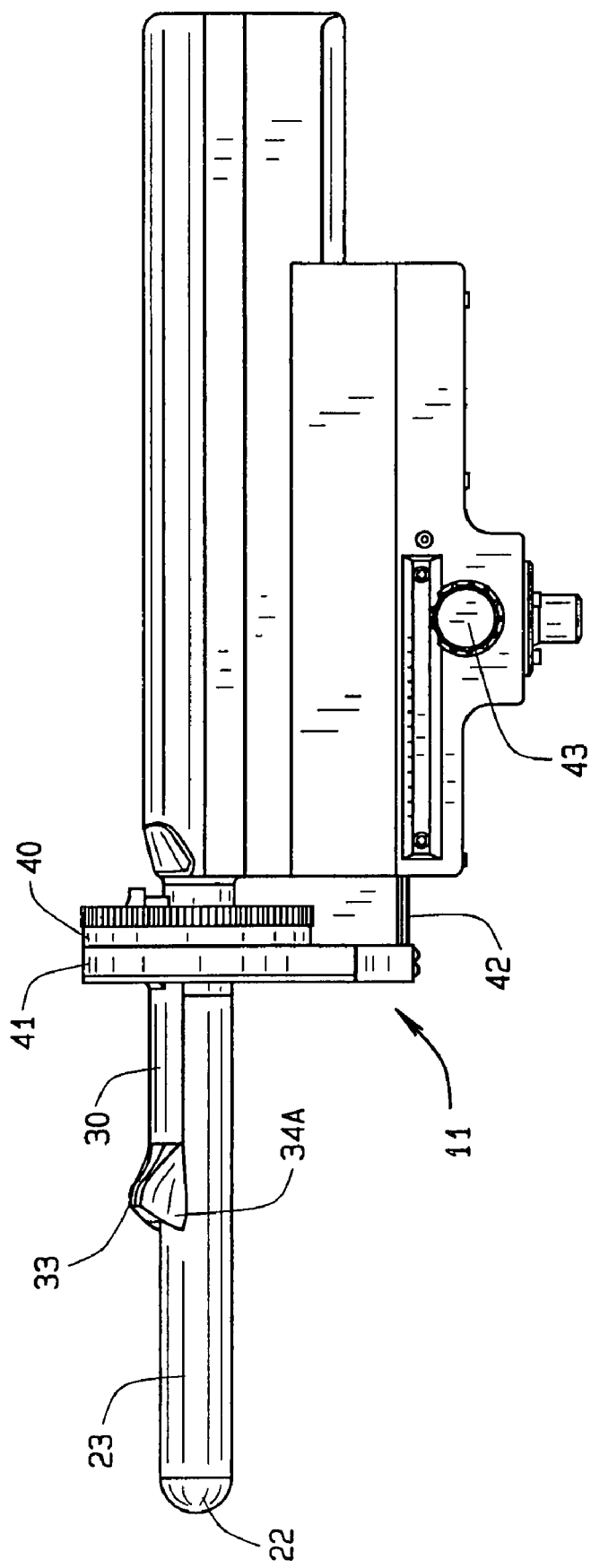

TARGETED BIOPSY DELIVERY SYSTEM

CROSS REFERENCE TO RELATED APPLICATION

This continuation patent application claims priority to the nonprovisional patent application having Ser. No. 10/842,652, which was filed on May 10, 2004 now abandoned which claims priority to the provisional patent application having Ser. No. 60/494,910, which was filed on Aug. 13, 2003.

BACKGROUND OF THE INVENTION

Prostate health is a significant concern for men over the age of fifty. If prostate cancer is suspected from either a physical examination or because of a Prostate Specific Antigens test, a biopsy is performed to collect tissue samples from the prostate for evaluation by a pathologist. Prostate tumors are small growths scattered about the prostate. For this reason, a physician will take multiple tissue samples from different areas of the prostate, typically between 9 and 18 samples.

The normal procedure for obtaining biopsy samples with ultrasound guidance is called Transrectal Ultrasound (TRUS) Guided Prostate Biopsy. An end-fire ultrasound probe is used, which generates a pie-shaped image plane. Some end-fire probes are manufactured with a biopsy needle channel, which passes through the body of the probe at an angle, such that a biopsy needle set inserted through the biopsy needle channel exits the channel at a slight angle relative to the body of the probe. Most probes require a needle set guide tube to be affixed to the probe body, such that a needle set placed through the guide tube parallels the axis of the probe and the needle set can be extended beyond the end of the probe. In use for both, the physician inserts the ultrasound probe into the rectum, and moves the probe around until the specific area of the prostate to be sampled is identified. The physician then bends the probe upward, pointing the biopsy needle channel or biopsy needle set guide at the targeted area of the prostate. A needle set is inserted into and through the needle channel or guide, pushed through the rectum wall and into the prostate.

Standard coring biopsy needles sets are made from substantially rigid, coaxially aligned, stainless steel wire and tubing. They are comprised of two basic components; an inner solid wire stylet with specimen notch and a hollow outer cutting cannula. Once the needle set is correctly positioned relative to the area of tissue to be sampled, the inner stylet is quickly advanced under spring loaded or similar pressure into the prostate tissue. The tissue to be sampled then "prolapses" into stylet's sample notch cutout. Almost instantaneously the outer cutting cannula quickly advances, also under spring loaded pressure, which serves to sever and capture the tissue that had prolapsed into the stylet notch. The needle set is then removed from the tissue/patient so that the tissue sample can be extracted from the needle set and evaluated for the presence of cancer. The physician then moves the probe around within the rectum to identify the next area of the prostate to be sampled, and the process is repeated. As noted, between 9 and 18 samples are typically taken from different areas of the prostate.

Existing biopsy methods suffer from a number of disadvantages. Because the probe must be physically moved about within the rectum by hand to identify and target the different areas of the prostate, it is difficult for physicians to precisely targeted biopsy sample locations, often causing the need for additional samples to be taken. Further, if a sample seems to confirm cancer, it is difficult for the physician to accurately know where in the prostate the sample was taken from, and so difficult to re-biopsy the same tissue location to confirm the cancer.

A number of systems or devices have been proposed for the purpose of better targeting biopsies. Batten, et al, (U.S. Pat. No. 5,398,690) discloses a slaved biopsy device, analysis apparatus, and process. In Batten, an ultrasound device is inserted into the male urinary tract through the penis, with the biopsy and treatment device inserted transrectally. Chin, et al, (U.S. Pat. No. 6,179,249) discloses an ultrasound guided therapeutic and diagnostic device. Chin is a flexible ultrasound device used for laproscopic surgery. Lin (U.S. Pat. No. 6,261,234) disclosed a method and apparatus for ultrasound imaging with biplane instrument guidance. Lin's ultrasound device uses two transducers to create two image planes, and has a biopsy needle guide which directs a biopsy needle at the intersection of the imaging planes. Burney, et al (U.S. Pat. No. 6,447,477) discloses surgical and pharmaceutical site access guide and methods. Burney shows a biopsy device in which a thick needle with side exit ports is inserted into the targeted tissue. Biopsy needles are then inserted into the thick needle, exiting out the side to take samples. Further, a number of systems have specified the use of flexible biopsy needle kits.

However, all of these inventions suffer from a number of disadvantages. All require specialized equipment, and do not make use of existing ultrasound systems and technology. All require the movement of the imaging device, making it more difficult to plan and target areas of the prostate for biopsy. Further, the flexible biopsy needles called out either require heating or additional force to cause them to fire, and are impractical for use with established prostate biopsy procedures and existing biopsy needle set firing devices.

Therefore, users would benefit from a biopsy system to allow a biopsy to be planned prior to the tissue sampling, to allow the biopsy needle to be precisely inserted into a targeted area and which is able to record the precise location from which the tissue sample is collected while the imaging device remains stationary. Users would also benefit from a flexible needle set which may be easily "fired" while in a curved position. Further, users would benefit from a means of precisely delivering a treatment to a targeted area of an organ or tissue mass.

SUMMARY OF THE INVENTION

It is the principal object of this invention to provide a device and method for precisely planning, undertaking and recording a multi-sample biopsy of a targeted tissue mass such as a prostate, improving physicians' ability to diagnose cancer.

Another object of the invention is to allow a biopsy plan to be formulated identifying the specific quadrants and areas of the prostate to be sampled.

Another object of the invention is to allow this biopsy plan to be saved as a reference point.

Another object of the invention is to allow a physician to adjust the biopsy needle guide to allow the physician to precisely insert the needle into the tissue at the planned location.

Another object of the invention is to allow a physician to monitor the needle set as it is inserted into the tissue, to verify that the needle is in the planned location.

Another object of the invention is to provide a biopsy needle guide which can be affixed to or associated with existing side-imaging transrectal ultrasound probes.

A further object of the invention is to allow the transrectal ultrasound probe to remain stationary while the biopsy samples are gathered from different areas of the prostate, thereby improving the accuracy of the procedure.

A further object of the invention is to allow the probe to remain stationary while the needle guide is moved longitudinally along the probe and is also rotated around the probe.

A further object of the invention is to provide a needle set guide which can redirect the needle set such that the needle set can be curved while still maintaining the freedom of movement to allow the firing and collecting of tissue samples.

A further object of the invention is to provide a biopsy needle set that may be redirected at an angle and further maintains its ability to be fired and so collect the tissue samples.

An object of an alternative embodiment of the invention is to allow a treatment plan to be formulated identifying the specific areas of tissue or an organ to be treated.

A further object of an alternative embodiment of the invention is to allow this treatment plan to be saved as a reference point.

Another object of an alternative embodiment of the invention is to allow a physician to precisely insert a needle or treatment delivery means into the tissue at the planned location.

Another object of the invention is to allow a physician to monitor the needle or treatment delivery method as it is inserted into the tissue, to verify that the needle or treatment delivery method is in the planned location.

These and other objects, advantages and features are accomplished according to the devices and methods of the following description of the preferred embodiment of the invention.

As noted the present invention relates to a biopsy targeting system for use with ultrasound imaging devices, and particularly for use in sampling prostate tissue. The biopsy targeting system consists of a redirecting biopsy needle guide which works in conjunction with a side-view or end-fire transrectal ultrasound probe, a cooperating software program which can be loaded and operated on a computer controlled ultrasound system, and a bendable needle set.

In use, the transrectal ultrasound probe is placed in the cradle of a stabilizer. The redirecting needle guide positioning assembly is also affixed to the cradle. The physician then advances and adjusts the cradle to allow the transrectal probe to be inserted into the rectum of a patient. The physician generates an ultrasound image while positioning the probe to insure that the patient's prostate is viewable within the viewing area of the probe. Once the probe is correctly positioned, the physician then locks the probe in place in the stabilizer.

With the transectal probe in place, the physician initiates a full 3D scan of the prostate. The multiple image slices are captured by the ultrasound system. The physician then looks through these saved images, to identify possible problem areas of the prostate and further to decide which areas of the prostate to sample. Typically, physicians collect 9 to 18 tissue samples from different areas of the prostate. As part of this process, the physician is able to use the software program to project potential needle path lines onto the images of the prostate. These paths are shown as lines in views parallel to the needle path and as circles where the paths pierce the image plane. Each possible path is described by the positional settings of the redirecting needle guide. When the physician identifies a specific area to be sampled, the physician moves a projected needle path line to intersect the planed area to be biopsied. The physician continues to evaluate the prostate and target additional areas for sampling, again saving projected needle paths for each planned sample. Further, if the physician does not identify any possible problem areas, but wishes to take a standard biopsy, the physician can use a range of default setting on the computer program to project between 9 and 18 projected needle paths with a standard distribution throughout the prostate.

Once the biopsy is planned, the physician initiates the biopsy. All of the needle paths for a given longitudinal image are displayed on the ultrasound monitor. The display shows the coordinates of the planned needle paths which correlate to the positional setting of the redirecting needle guide. The physician then advances and/or rotates the redirecting needle guide to the correlating coordinates for the first planned needle path. The physician then inserts a flexible biopsy needle kit into the redirecting needle guide's needle insertion point. The needle set is advanced by hand through the needle set channel, including through the redirecting curve within the needle guide. This redirecting curve causes the needle to exit the needle guide, within the rectum of the patient, at an angle relative to the transrectal probe. The physician pushes the needle guide through the tissue of the rectal wall and into the prostate, monitoring the progress of the needle on the ultrasound system and insuring that the actual path of the needle matches the planned needle path being projected on the image. When the biopsy needle set has achieved the correct depth of penetration, the physician uses a standard biopsy firing gun to "fire" the needle set, causing the stylet and cannula to quickly extend in sequence, cutting and capturing a slice of prostate tissue in the specimen notch of the needle set. Because the specimen notch is substantially longer than in standard biopsy needles and the cannula body is flexible, the needle set is very flexible and able to be fired even though bent. The specimen notch is extended to the curved portion of the needle set within the redirecting needle set guide, allowing the stylet to be quickly moved in reference to the cannula without binding. With the needle still in the prostate, the physician saves the ultrasound image(s) on the computer program, creating a permanent record of the biopsy tissue location. The physician then removes the biopsy needle with captured tissue sample. Once removed, the cannula is retracted from the stylet, allowing the tissue sample to be placed into a tissue specimen dish. The physician then advances or moves the redirecting biopsy needle guide to the next planned needle path location, and repeats the procedure.

BRIEF DESCRIPTION OF THE DRAWINGS

FIG. 3 is a side view of the redirecting needle set guide mounted on a side-imaging transrectal ultrasound probe, showing the guide positioning assembly.

FIG. 23 is a side view of the redirecting guide with a flexible needle set inserted and extending out of the guide such that the needle set is bent by the needle set channel bend.

PARTS NUMBERS

Figure 1:
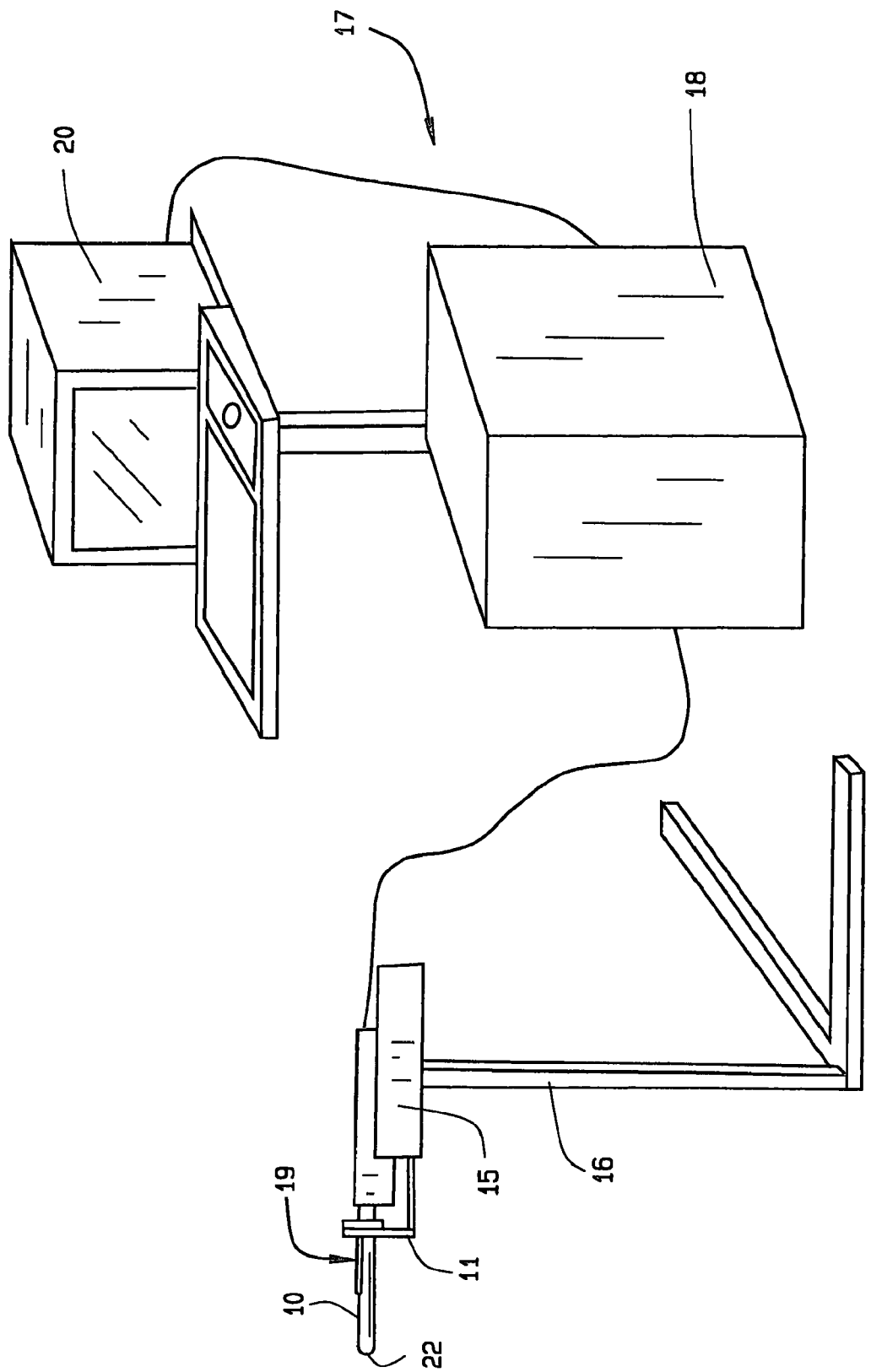
FIG. 1 is a perspective view of targetable biopsy system in conjunction with an ultrasound imaging system and stabilizer.

Rectum 1
Prostate 2
redirecting guide 10
alternative redirecting guide 10A
positioning assembly 11
targeting software system 12
flexible needle set 13
cradle 15
stabilizer 16
ultrasound system 17
ultrasound system CPU 18
side view transrectal probe 19
monitor 20
probe tip 22
probe imaging window 23
guide body 30
needle set channel 31
needle set insertion point 32
needle set exit point 33
front body guide extensions 34A, 34B
imaging cutout 35
needle set channel bend 36
enlarged bend channel 37
insertable metal tube 38
rotational adjustment collar 40
fixed collar 41
longitudinal slides 42
longitudinal position controller 43
needle path location registry 50
needle path lines 51
needle path dots 52
flexible stylet 60
flexible cannula 61
tip 62
extended specimen notch 63
stylet body 64
cutting tip 65
cannula body 66
counter bore and taper 67
bending notches 70
tiered specimen notch 71
segmented specimen notch 72
removable needle set guide insert 75
stylet hub 76
cannula hub 77
strip 78
depth markings 79
cannula sheath 81
spiral cut 82
non-spiral cut portion 83
beveled edge 84
Biopsy attachment angle selector 201 and display
Biopsy attachment depth selector 202 and display
needle path coordinates display 204 window
Finished with Biopsy Planning 206 button
Remove selected biopsy location 207 from plan button
Add selected biopsy location to 208 plan button
Select pre-planned template 209
Sagittal image plane selector 210
Transverse image plane selector 211
Transverse image display 212
Sagittal Image display 213

DESCRIPTION OF THE PREFERRED EMBODIMENT

Figure 2:
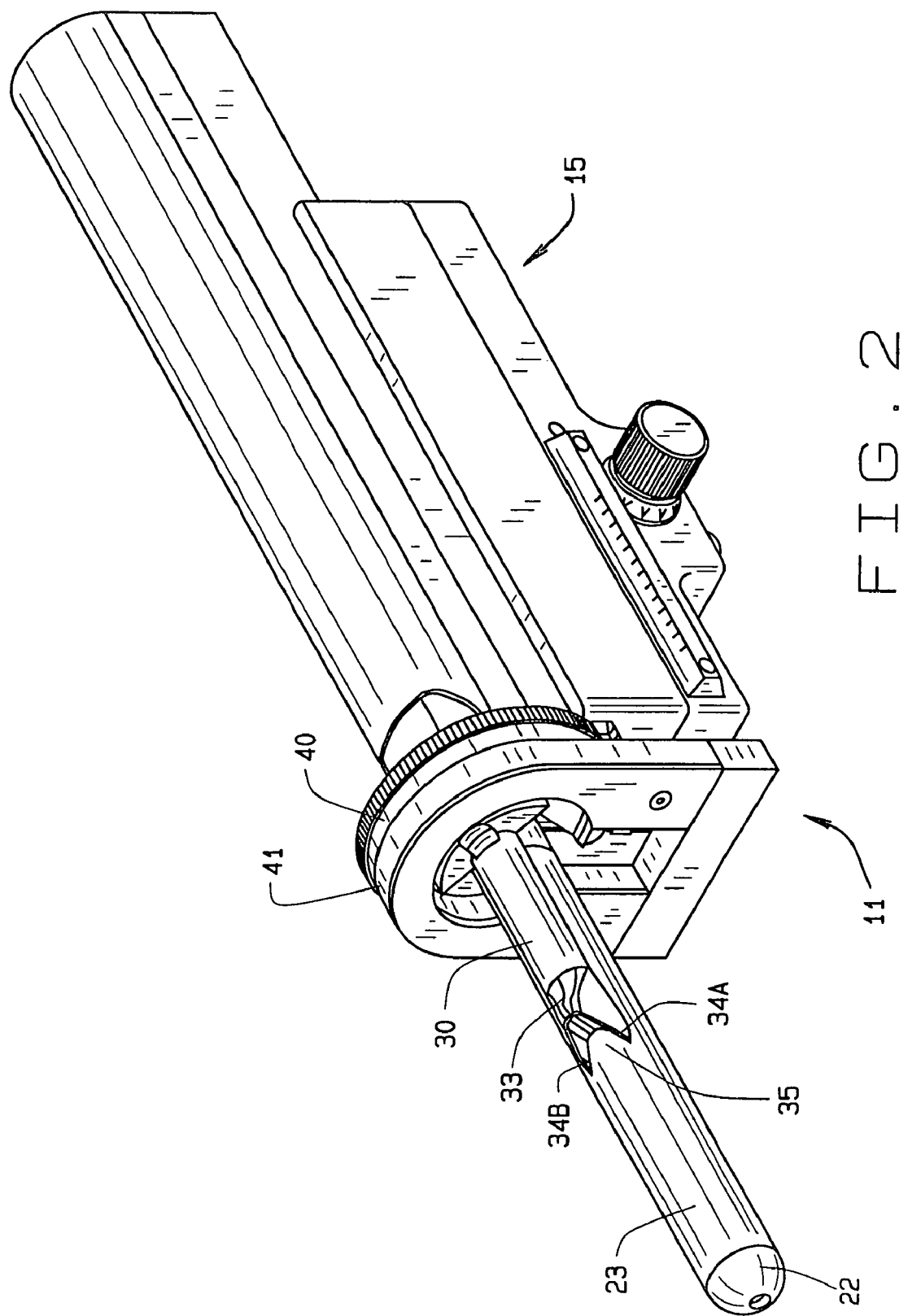
FIG. 2 is a perspective view of the redirecting needle set guide mounted on a side-imaging transrectal ultrasound probe.
Figure 3A:
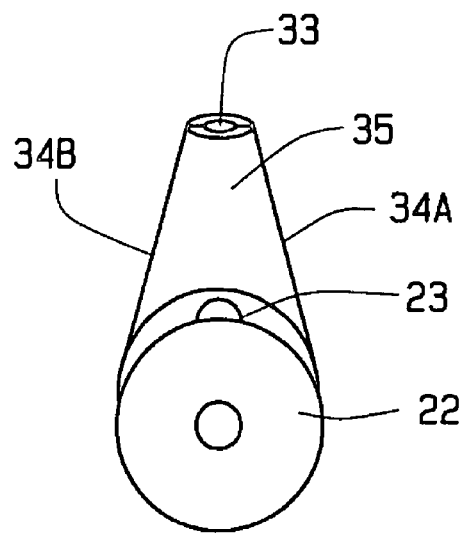
FIG. 3A is a front view of the redirecting needle set guide mounted on a side-imaging transrectal ultrasound probe in the manner shown in FIGS. 1, 2 and 3.
Figure 7:
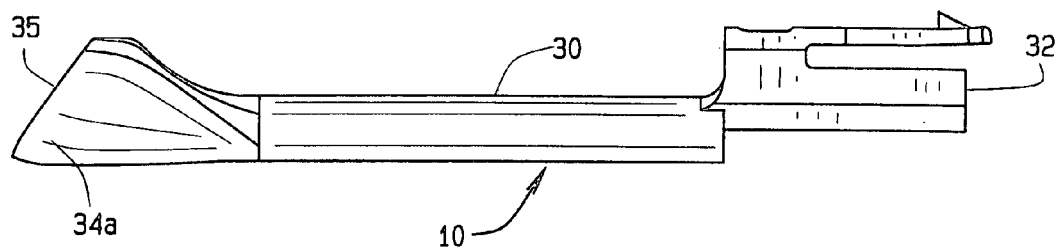
FIG. 7 is a side view of an embodiment of the targetable biopsy guide.
Figure 8:
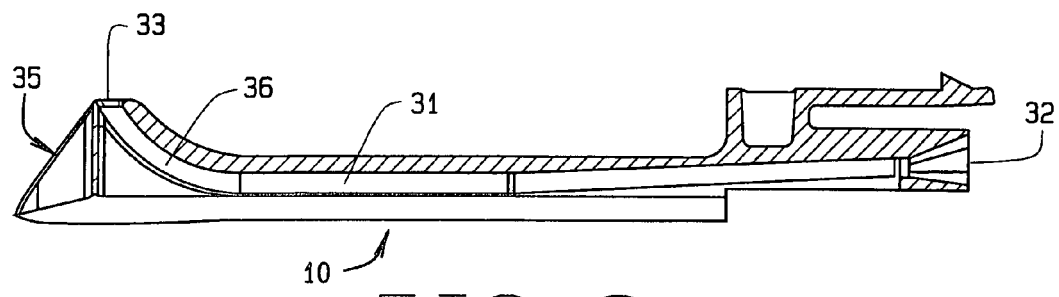
FIG. 8 is a side cutaway view of an embodiment of the targetable biopsy guide designed to be manufactured with an insertable metal tube.
Figure 9:
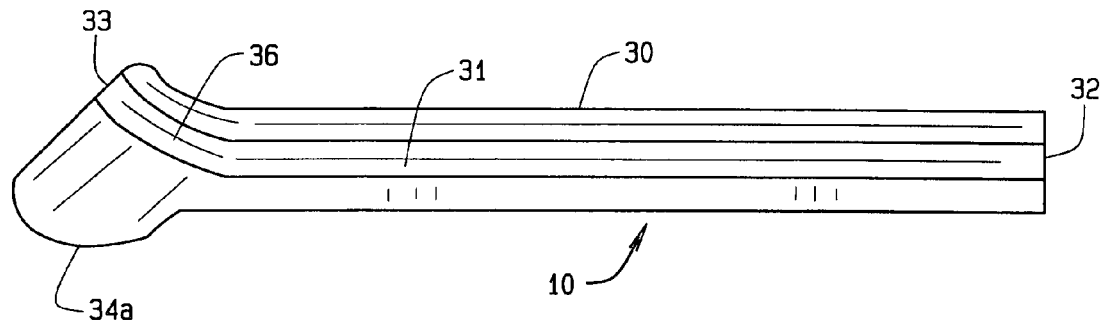
FIG. 9 is a side cutaway view of an alternative embodiment of the targetable biopsy guide.
Figure 10:
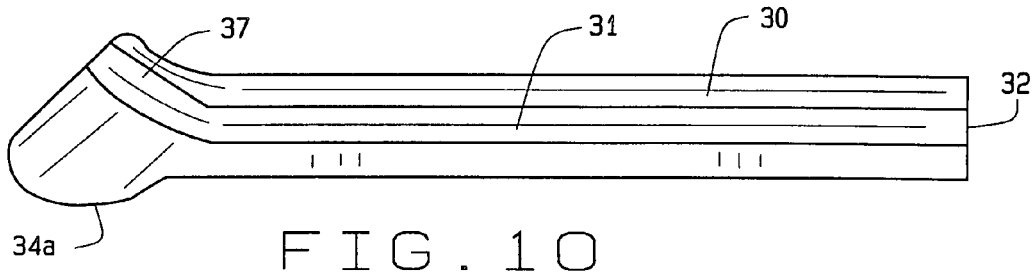
FIG. 10 is a side cutaway view of an alternative embodiment of the targetable biopsy guide with an enlarged bend channel.
Figure 20:
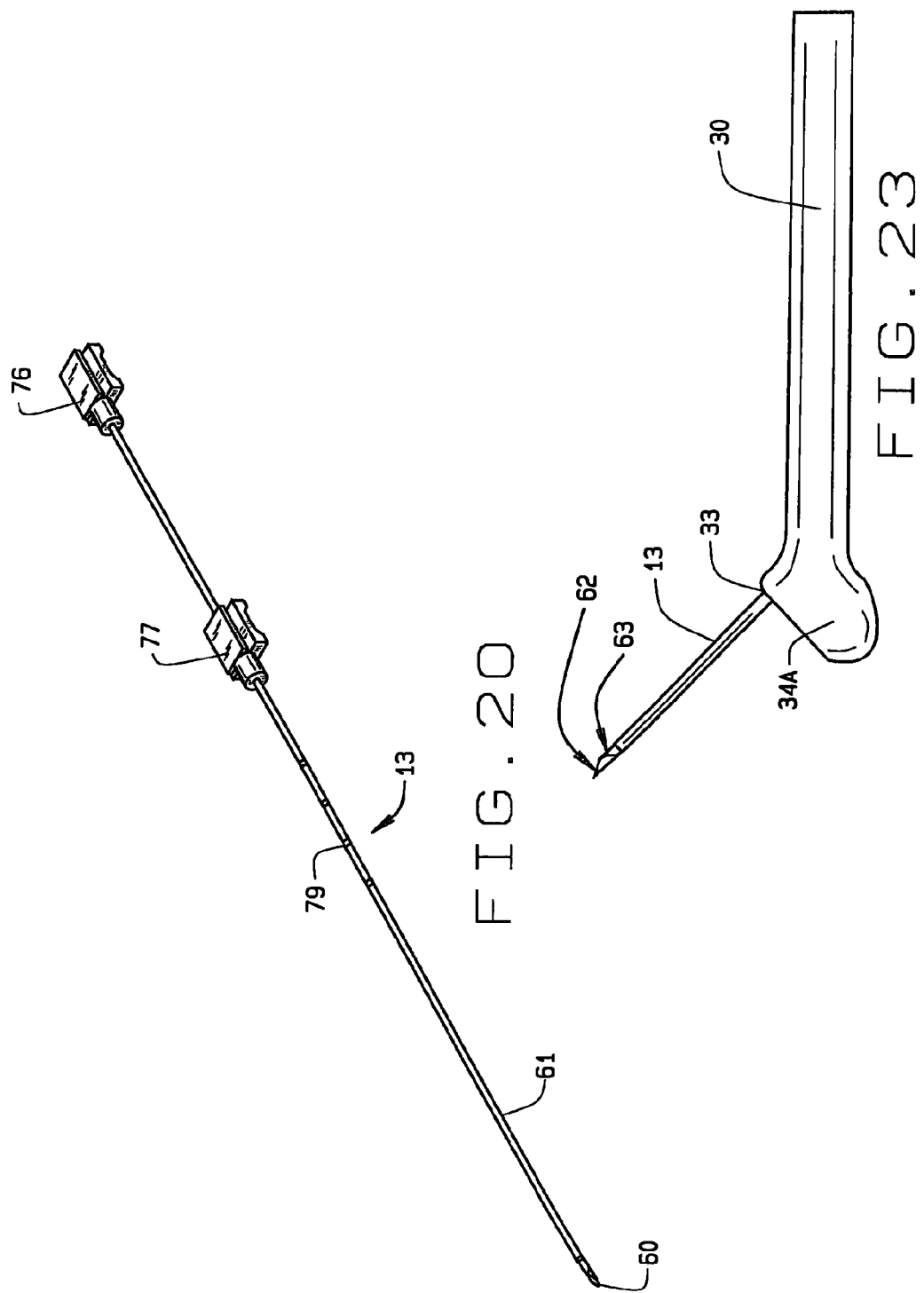
FIG. 20 shows a perspective view of an embodiment of the flexible needle set.

As seen in FIG. 1, the targeted biopsy system is comprised of a redirecting guide 10, positioning assembly 11, targeting software system 12 (loaded on CPU 18) and flexible needle set 13 (best seen in FIG. 20). The positioning assembly 11 is affixed to cradle 15, which is a part of stepper and stabilizer 16. Working in conjunction with the targeted biopsy system is ultrasound system 17, which is comprised of ultrasound system CPU 18, side view transrectal probe 19 and monitor 20. Side view transrectal probe is comprised of probe tip 22 and probe imaging window 23. As seen in FIGS. 2, 3A and 7, the redirecting guide 10 consists of guide body 30, needle set channel 31, needle set insertion point 32, and needle set exit point 33, front body guide extensions 34A and 34B, imaging cutout 35. As seen in FIG. 10, needle set channel 31 may be provided with enlarged bend channel 37. As seen in FIG. 8, the redirecting guide 10 may be provided with insertable metal tube 38. In an alternative embodiment, the redirecting guide may contain one or more pathways may be used for insertion of the biopsy needle kit. The redirecting guide may be comprised of a movable device such that the opening through which the needle kit exits may be moved relative to the opening into which the biopsy needle kit is placed. In a further alternative embodiment, the redirecting guide may straighten a previously curved biopsy needle kit such that the biopsy needle kit re-curve when leaving the redirecting guide.

As best seen in FIG. 3, positioning assembly 11 is comprised of rotational adjustment collar 40, fixed collar 41, longitudinal slides 42 and longitudinal position controller 43.

Figure 4:
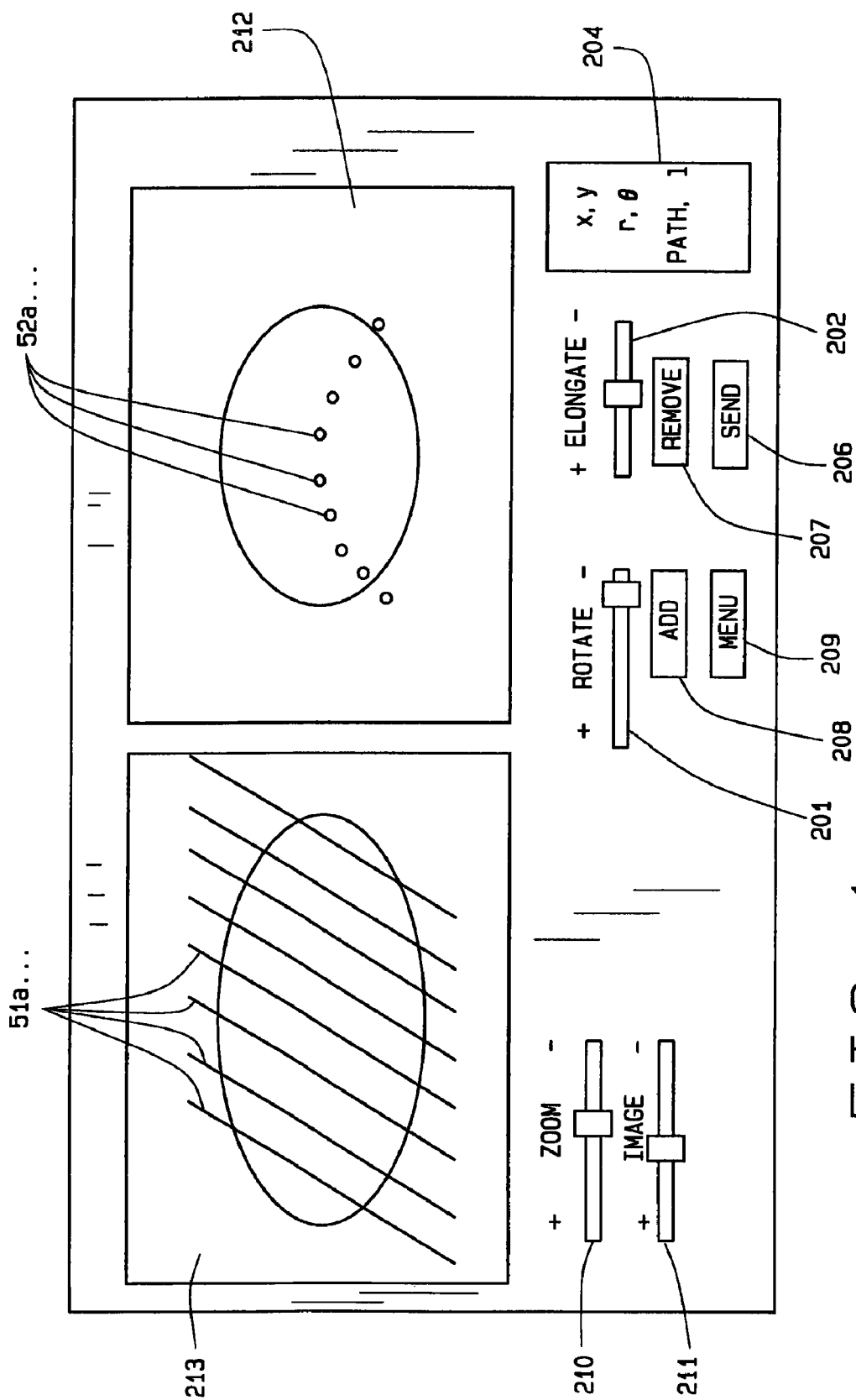
FIG. 4 is a planning software interface displayed on the monitor.

As best seen in FIG. 4, targeting software system 12 is comprised of transverse image display 212, Sagittal Image display 213, longitudinal projected needle paths 51a, b, c, etc and transverse projected needle paths 52a, b, c, etc., in addition to various controls.

Figure 14A:
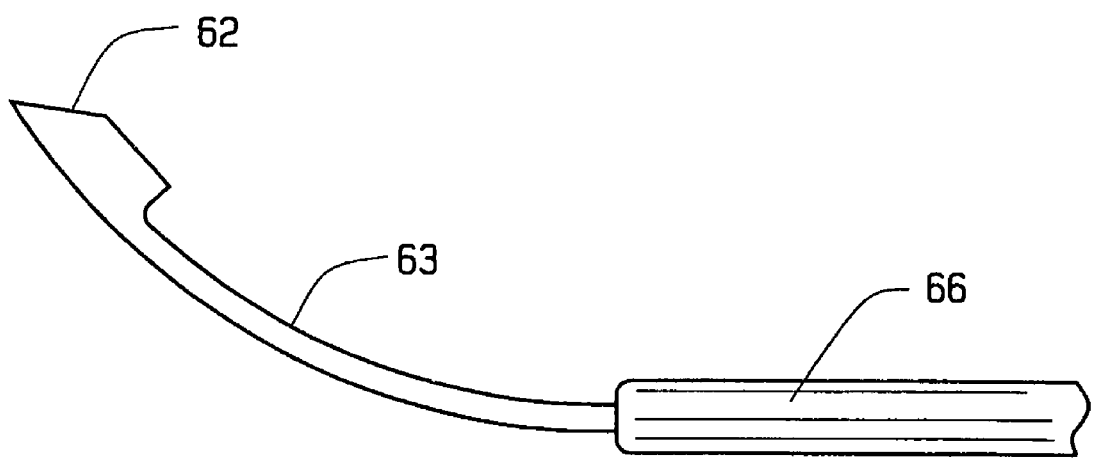
FIG. 14A is a side view of a flexible biopsy needle set in accordance with the present invention.
Figure 11:
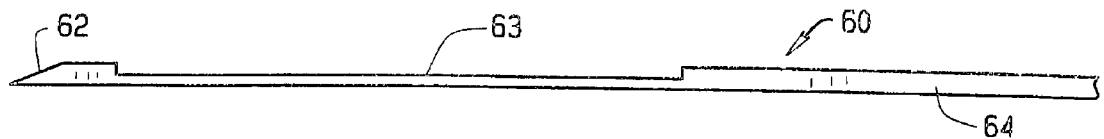
FIG. 11 shows a side view of a biopsy stylet with extended specimen notch.
Figure 12:
FIG. 12 shows a side view of an alternative embodiment of the stylet with dual extended specimen notches.
Figure 13:
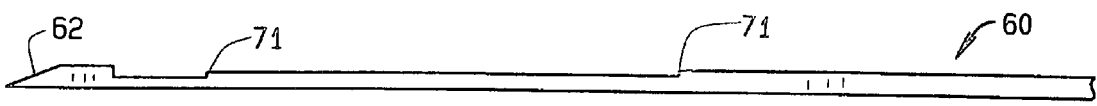
FIG. 13 shows a side view of an alternative embodiment of the stylet with a tiered specimen notch.
Figure 14:
FIG. 14 shows a side view of an alternate embodiment of the stylet with multiple notches to facilitate bending.

As best seen in FIG. 20, flexible needle set 13 consists of flexible stylet 60 and flexible cannula 61. Stylet 60 may be affixed to stylet hub 76, with cannula 61 affixed to cannula hub 77. Further, cannula 61 may be provided with depth markings 79. As seen in FIGS. 11 and 14A, the preferred flexible stylet 60 consists of tip 62, extended specimen notch 63 and stylet body 64 that is surrounded by the cannula body 66. As seen in FIG. 12, an alternative preferred flexible stylet 60 consists of tip 62 and segmented specimen notches 72a and 72b. Alternative embodiments of flexible stylet 60, as seen in FIGS. 13 and 14, contain bending notches 70 and tiered specimen notch 71.

Figure 15:
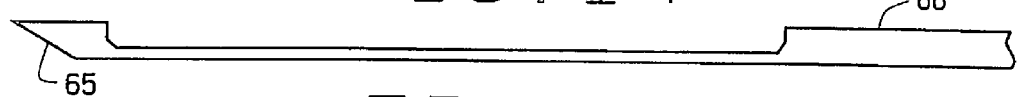
FIG. 15 shows a side view of an embodiment of the cannula in which the cannula tube has been ground down along its length to leave a flexible spine.
Figure 16:
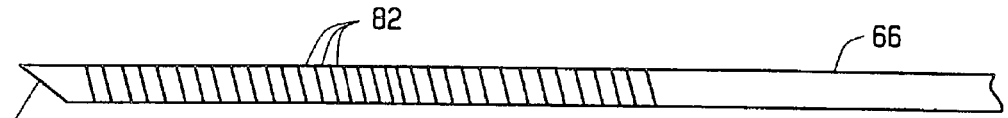
FIG. 16 shows a side view of an embodiment of the cannula in which the cannula tube has been spiral-cut along its length to facilitate bending of the cannula.
Figure 17:
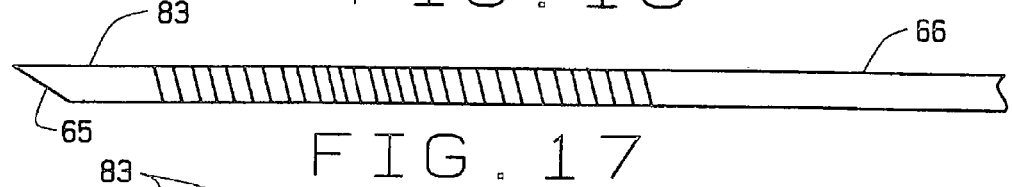
FIG. 17 shows a side view of an alternative embodiment of the cannula in which the tip of the cannula tube is uncut while the body of the cannula tube has been spiral-cut.
Figure 18:
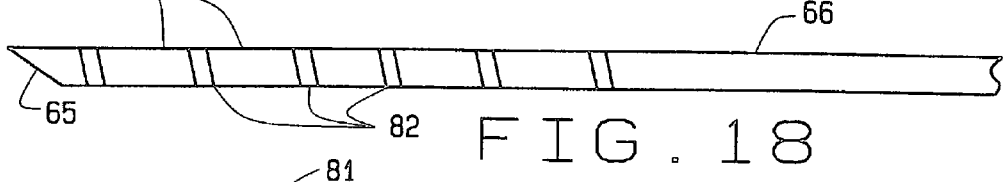
FIG. 18 shows a side view of an alternative embodiment of the cannula in which sections of the cannula tube alternate between cut and uncut.
Figure 19:
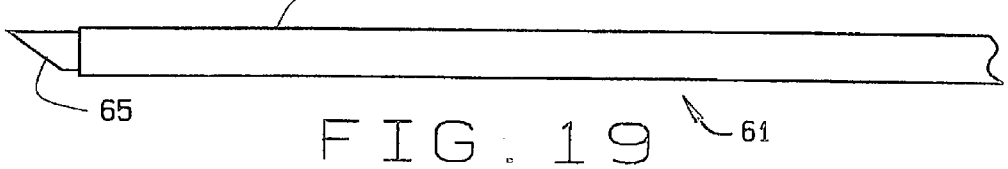
FIG. 19 shows a side view of an embodiment of the cannula in which the cannula tube is encased in flexible tubing.

As seen in FIG. 19, the preferred embodiment of cannula 61 consists of cutting tip 65, cannula body 66 and cannula sheath 81. The cannula sheath may have beveled edges. As seen in FIG. 15, a portion of the body of flexible cannula 61 has been removed. As seen in FIG. 16, cannula body 66 may be provided with spiral cut 82 to facilitate bending. As seen in FIG. 17, in an alternative embodiment of cannula 61, cannula body 66 may be provided with non-spiral cut portion 83 at cutting tip 65, to facilitate the straight entry of the cannula into the tissue. As seen in FIG. 18, in a further alternative embodiment of cannula 61, cannula body 66 may be provided with non-spiral cut portions 83 interspersed with spiral cuts 82. In an alternative embodiment of flexible cannula 61 consists of a cutting tip inserted into the flexible cannula body.

It should be noted that both the stylet cannula can be made from a range of flexible materials, including combinations of one or more materials, to facilitate the bendability. This may include traditional materials used in medical devices, such as stainless steel, as well as materials such an nitinol®. Furthermore, the cannula design may mirror the stylet, such that portion or portions of the metal cannula tube are removed to create a metal component which has a metal cutting tip, a long spine consisting of only a portion of the cannula wall in the flexible part of the cannula and then the full tubular cannula. Furthermore, the machine cannula may be partially or wholly incased in a cannula sheath, which may be plastic or some other material.

Figure 21:
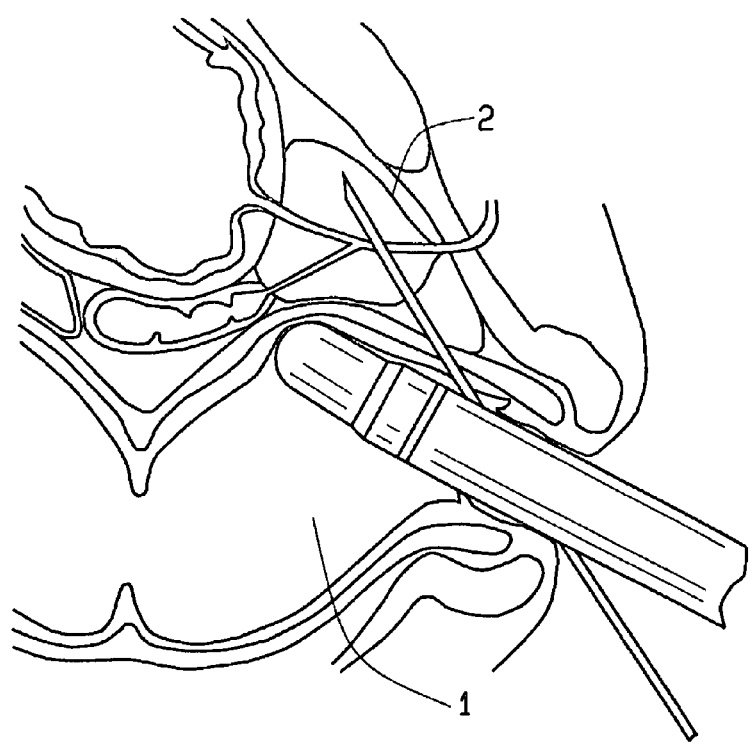
FIG. 21 is a side view of the traditional method of taking a prostate biopsy with a biopsy needle channel.

FIG. 21 shows a biopsy being performed using the standard method, using an end-fire ultrasound probe with a biopsy needle channel. The probe is inserted into the rectum, and then angled upward until the probe tip is pointed at the desired portion of the prostate. A needle set is then inserted through the biopsy needle channel guide into the prostate 2.

Figure 22:
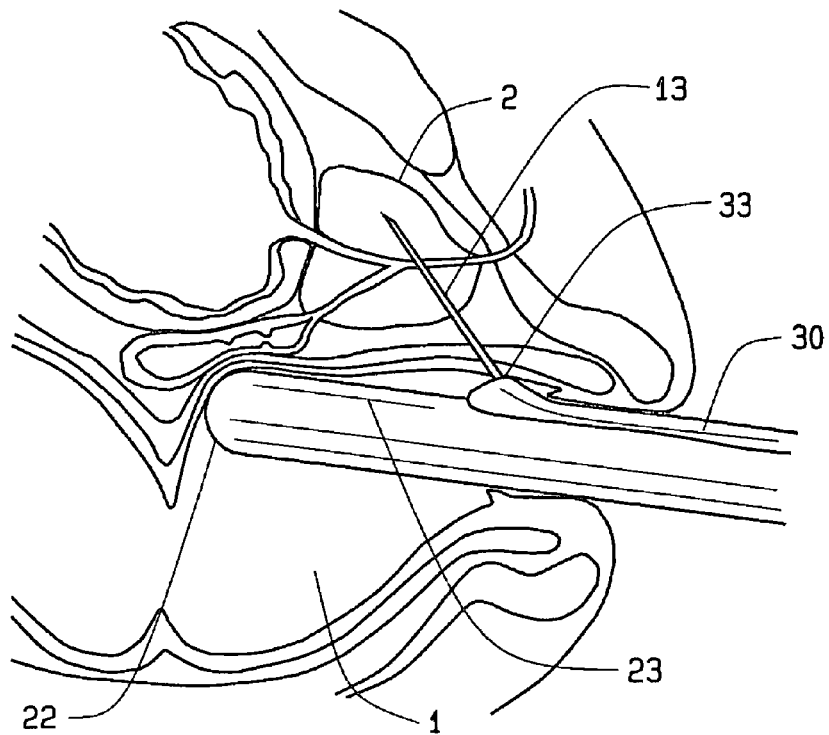
FIG. 22 is a side view of the bendable needle and biopsy targeting system mounted on a side-fired probe taking a biopsy.

In use of the preferred embodiment of the invention, as seen in FIGS. 1 and 22, side view transrectal probe 19 is mounted on the cradle 15 of a stabilizer 16. Redirecting guide 10 is also mounted on the cradle 15, such that guide body 30 sits atop probe tip 22. As seen in FIG. 2, front body extensions 34a and 34b partially wrap around probe tip 22 to help maintain the guide body 30 on the probe tip 22. The cradle 15 is moved forward, with the probe tip 22 inserted into patient's rectum 1. Probe tip 22 is generating ultrasound images, which are displayed on monitor 20. The physician uses this image to insure that the entirety of prostate 2 is viewable by probe imaging window 23. Once the probe tip 22 is correctly positioned, the physician locks in place cradle 15.

Figure 5:
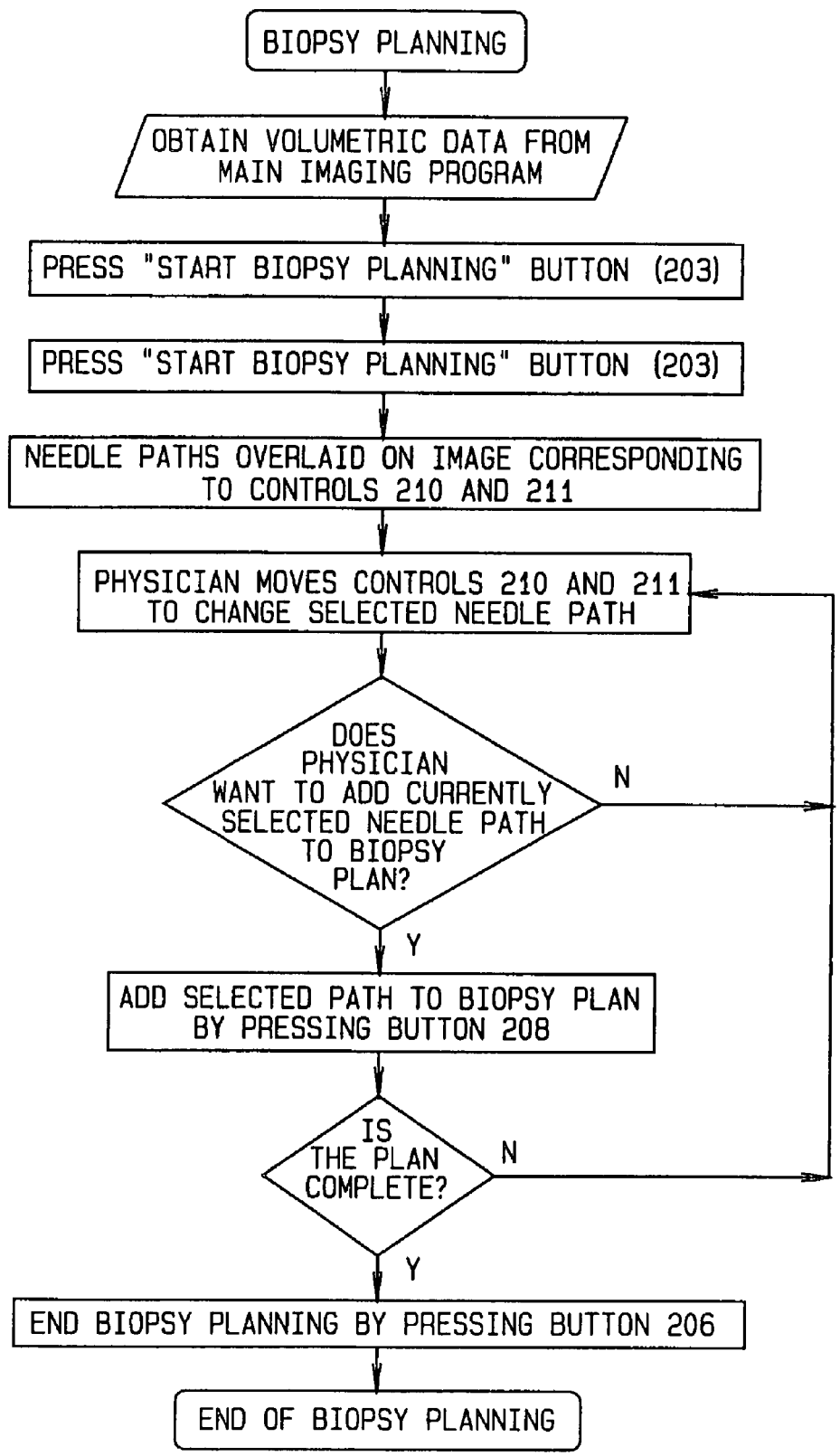
FIG. 5 is a schematic of the biopsy planning process.

The biopsy planning process is illustrated in FIG. 5. A representative display of the biopsy information to the user is shown in FIG. 4. The process begins with the planning software obtaining a set of volumetric data 101. The volumetric data consists of two sets of sampled images. One set is of longitudinal images sampled at a regular angular spacing, and the other is a set of transverse images sampled at regular depth spacing. If only one of the two sets is available, one may be interpolated from the other. The physician starts the planning process by pressing button 203 to satisfy step 102 of FIG. 4. For 103, the planning system overlays a series of lines 51a, b, c, etc. and dots 52a, b, c, etc. on the images in panes 212 and 213. These lines and dots represent the available needle paths selectable with controls 40 and 43, and show where the needle intersects with image planes. Each line and dot combination is labeled with a coordinate 50 corresponding to a unique pair of setting for controls 40 and 43. The user can review the stored images using controls 210 and 211 to change the image viewed. For 104, the user can "simulate" the effect of controls 40 and 43 using on-screen controls 201 and 202 to adjust the selected needle path. The current path is displayed by changing the color of the appropriate line and dot (51 and 52, respectively). The user adds a specific needle path to the biopsy plan (105) by selecting button 208. Each time a path is selected, a record is placed into needle path coordinates display window 204 showing the coordinates of the path. The user may also remove a specific path from the plan by selecting button 207. When the plan is complete, the user clicks on the button 206 to send the planning process (106).

Figure 6:
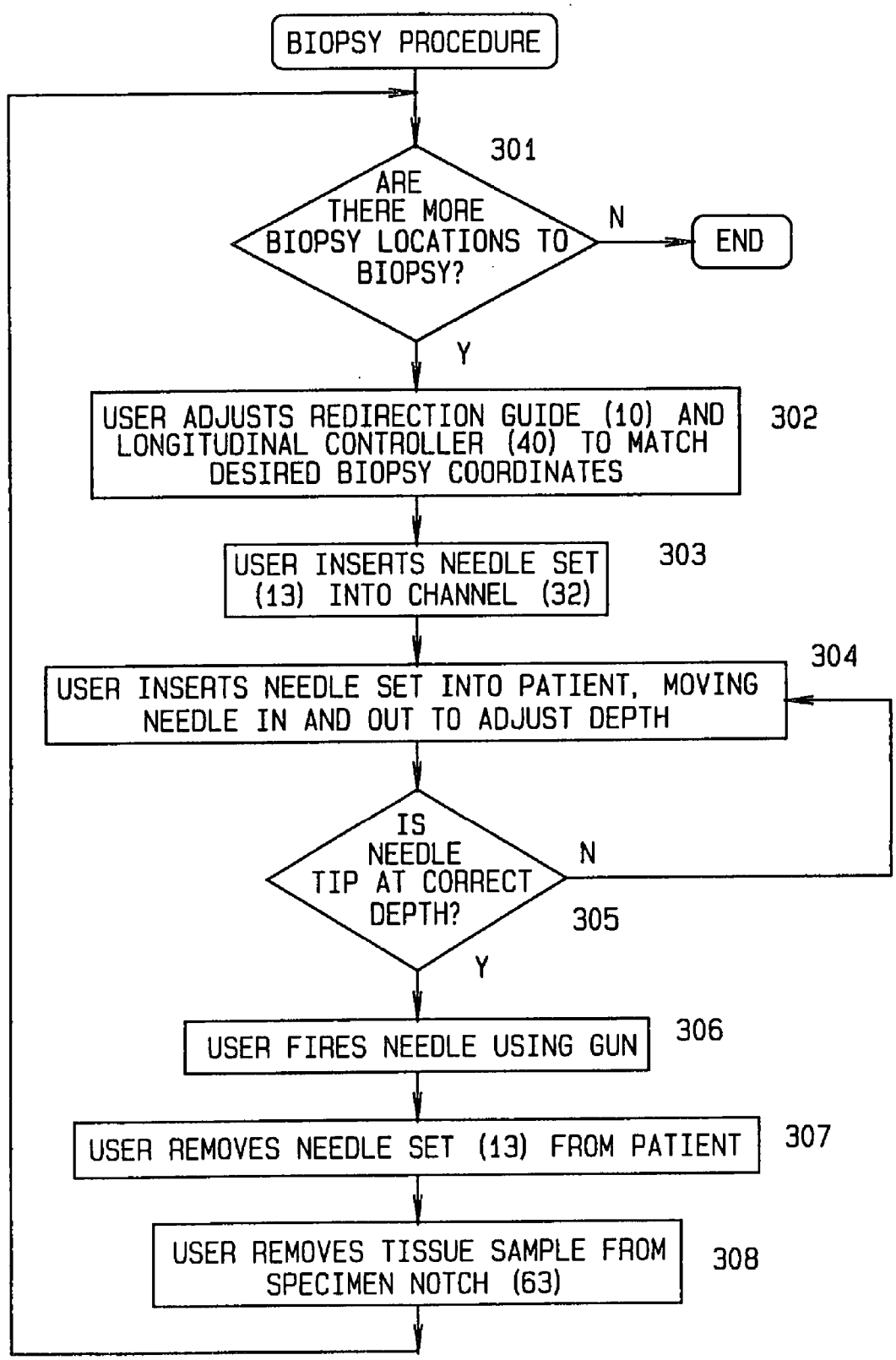
FIG. 6 is a schematic of the biopsy procedure.

Once the biopsy planning process has been completed, the physician or technician may then proceed with the biopsy procedure, to complete the series of precision located biopsy's to be taken through the usage of this instrument. For example, as can be noted in FIG. 6, once a biopsy procedure has been completed, the physician then determines whether any more biopsies are needed, and where the biopsy locations may be determined. This can be seen at 301. If no additional biopsies are required, this is the end of the procedure. If additional biopsies are considered as needed, the physician then adjusts the redirection of the guide 10, and the longitudinal controller 40, to mass the desired biopsy coordinates, as provided upon the scanner. This can be noted at 302. Then, the user inserts a needle set 13 into the channel 32, to prepare for additional biopsies. The physician then inserts the needle into the patient, moving the needle in and out to adjust for depth, as determined by the scanner, as can be seen at 304. Then, the physician can determine if the needle tip is at the correct depth, at 305. If it is not, then the physician may move the needle and adjust its depth further. If it is, the physician then fires the needle of the biopsy instrument, as at 306. Then the physician removes the needle set 13 from the patient, having taken the biopsy as required. Then, the tissue sample is removed from the biopsy needle notch, for further analysis by the lab. This can be noted at 308. When this is completed, this concludes the conduct of biopsies upon the patient.

As alternative to the procedure in FIG. 4, preplanned biopsy selection menu 209 allows the user to select a predetermined needle pattern, typically 9-12 needle paths, without having to select each needle path manually. The needle paths generated could need to be adjusted for the specific size of the organ. The size of the organ can be input by various means. The planning process allows the physician to modify the needle paths as needed and to approve that they are correct.

Projected needle paths 51a, 51b, etc, include needle path location registry 50, which indicate the horizontal and rotational position of the needle path in reference to the probe. Working from the saved biopsy plan, displayed in 204, the physician rotates redirecting guide 10 using rotational adjustment collar 40, and then advances the redirecting guide using longitudinal position controller 40, both of which have position information which correlates to the needle path location registry 50. As seen in FIG. 8, the physician inserts flexible needle set 13 into needle set insertion point 32 and into needle set channel 31. When the needle set 13 reaches needle set channel bend 36, the needle set 13 is redirected at an angle away from the axis of probe tip 22. Needle set 13 exits needle set exit point 33. Because of imaging cutout 35, the physician is able to see the needle set in the ultrasound image as it exits exit point 33, allowing the physician to insure that the needle set 13 is in the path marked by projected needle path 51a. The physician monitors the depth of the needle set 13 as it is pushed through the rectum wall and into the prostate 2. Once the desired depth is reached, the physician stops inserting the needle set 13. Using a standard biopsy gun, the needle set 13 is "fired". This causes flexible stylet 60 to rapidly advance a short distance, such that tissue from the prostate two prolapses into extended specimen notch 63. Almost instantaneously flexible cannula 61 quickly advances, also under spring loaded pressure or other motivational means, which serves to sever and capture the tissue that had prolapsed into the extended specimen notch 63. Because the extended specimen notch 63 extends to the point where flexible needle set 13 is bent in needle set channel bend, the stylet and cannula are able to fire without the two pieces binding together, allowing the specimen to be effectively captured. The physician then removes the flexible needle set 13 with the captured specimen. The specimen is removed from the flexible needle set, and the physician then resets the redirecting guide to the coordinates of the next saved projected needle path 51b. The process is repeated until the physician has captured all of the samples as planned using the targeting software system 12.

FIG. 23 provides a side cut-away view of the redirecting guide with a flexible needle set inserted and extending out of the guide such that the extended specimen notch is bent by the needle set channel bend.

In an alternative embodiment of the invention, the invention is used to plan and perform a targeted treatment of an organ or tissue mass. With the device in place, the process begins with the planning software obtaining a set of volumetric data. The planning system overlays a series of needle path lines and needle path dots on the images in panes 212 and 213, which represent the available needle paths with coordinates that match the coordinates on rotational adjustment collar 40 and longitudinal position controller 43 of positioning assembly 11. The user selects specific needle paths, which are saved the treatment plan. Preplanned treatment selections allow the user to select a pre-determined needle pattern without having to select each needle path manually.

Working from the saved treatment plan, the physician rotates redirecting guide using rotational adjustment collar, and then advances the redirecting guide using longitudinal position controller, both of which have position information which correlates to the needle path location registry. The physician then inserts a flexible needle set or treatment delivery means into needle set insertion point 32 and into needle set channel 31. When the needle set or treatment delivery means reaches the needle set channel bend, the needle set or treatment delivery method is redirected at an angle away from the axis of probe tip 22. Needle set 13 exits needle set exit point 33. Because of imaging cutout 35, the physician is able to see the needle set or treatment delivery method in the ultrasound image as it exits exit point 33. The physician monitors the depth of the needle set or treatment delivery method as it is pushed into the targeted organ or tissue mass. Once the desired depth is reached, the physician is able to undertake the preferred activity. This may include using the delivery means to inject a solid, gas or liquid material or other treatment apparatus into the targeted organ or tissue mass. Further, the physician may insert an organism into the targeted organ or tissue mass. The material may be deposited and left in the targeted organ or tissue mass. Further, material previously deposited may be removed. The use of the deposited material may be as a treatment, a marker, or other uses. Further, the delivery means may be used to apply energy to a targeted organ or tissue mass, including but not limited to heat, cold, light and radiation. Once the treatment or marking is delivered, the physician then removes the flexible needle set or treatment delivery method, and then resets the redirecting guide to the coordinates of the next saved projected needle path. The physician has the option of saving the image of the treatment needle in the targeted organ or tissue mass, to record the location of the treatment as delivered. The process is repeated until the physician has treated or marked all of the targeted areas of the organ or tissue mass.

What is claimed is:

1. A system for biopsy of tissue of a mammalian body, the system comprising:

an ultrasonic probe having an elongate housing with an exterior surface configured and arranged to be received within a body cavity of the mammalian body, said elongate housing having a central longitudinal axis extending therethrough, and said ultrasonic probe configurable to scan longitudinal scan planes and transverse scan planes that pass through tissue adjacent the body cavity, said longitudinal scan planes through said longitudinal axis and said transverse scan planes orthogonal to said longitudinal axis;

a needle guide body concentrically mounted upon said exterior surface of said elongate housing of said ultrasonic probe, said needle guide body being rotatable about said longitudinal axis relative to said elongate housing and moveable along an axis parallel to said longitudinal axis relative to said elongate housing, and said needle guide body defining a needle guide channel that extends parallel to said longitudinal axis, said needle guide channel for guiding position and orientation of a flexible biopsy needle and cannula set passing therethough and exiting therefrom in order to take a biopsy of tissue adjacent the body cavity, wherein the flexible biopsy needle and cannula set includes a flexible biopsy needle surrounded by a flexible cannula; and a data processing system operably coupled to said ultrasonic probe, said data processing system including a display device and software system, said software system cooperating with said ultrasonic probe to display on said display device an image of one of said longitudinal scan planes and said transverse scan planes, wherein said software system is adapted to display said image in conjunction with guided movement of said flexible biopsy needle and cannula set through said guide channel of said needle guide body in order to monitor movement and position of said biopsy needle and cannula set within said body cavity.

2. The system according to claim 1 wherein said flexible biopsy needle comprises a flexible stylet containing an extended specimen notch.

3. The system according to claim 2 wherein said stylet and said cannula include a pre-formed curve.

4. The system according to claim 2 wherein said stylet and said cannula are manufactured from flexible material such as Nitinol®.

5. The system according to claim 2 wherein said stylet and said cannula exclude a pre-formed curve.

6. The system according to claim 2 wherein said stylet is assembled from two or more sections each made of materials with different properties to improve the flexibility.

7. The system according to claim 2 wherein said cannula is assembled from two or more sections each made of materials with different properties to improve the flexibility.

8. The system according to claim 2 wherein the length of said specimen notch is increased to improve the flexibility of the stylet.

9. The system according to claim 2 wherein multiple specimen notches are used to improve the flexibility of the stylet.

10. The system according to claim 9 wherein the depth of the specimen notches varies to improve the flexibility of the stylet.

11. The system according to claim 1 wherein said needle guide body is comprised of:
- an insertion point opening into said channel and into which a biopsy needle and cannula set may be inserted;
- an exit point opening out of said channel spaced away from said insertion point and through which a portion of the biopsy needle and cannula set exits;
- means for redirecting said biopsy needle and cannula set wherein said biopsy needle and cannula set outwardly of said exit point is angled relative to said biopsy needle and cannula set remaining outwardly of said insertion point; and,
- a means of positioning said biopsy needle guide body relative to said ultrasonic imaging probe.

12. The system according to claim 11 wherein said means of redirecting said biopsy needle and cannula set physically bends an initially straight biopsy needle and cannula set.

13. The system according to of claim 11 wherein said means of redirecting said biopsy needle and cannula set straightens an initially curved biopsy needle and cannula set wherein said biopsy needle and cannula set reacquires curvature upon exiting said guide body.

14. The system according to claim 11 wherein said means of redirecting said biopsy needle and cannula set is comprised of one or more static angled or curved channels.

15. The system according to claim 11 wherein said means of redirecting said biopsy needle and cannula set is comprised of a movable device that moves said exit point relative to said insertion point.

16. A system according to claim 1, wherein:
said biopsy needle and cannula of said biopsy needle and cannula set have a straight configuration, and said needle guide channel physically bends said biopsy needle and cannula into a bent configuration in conjunction with movement through said needle guide channel.

17. A system according to claim 1, wherein:
said biopsy needle and cannula of said biopsy needle and cannula set have a curved configuration, and said needle guide channel straightens said biopsy needle and cannula set into a straight configuration in conjunction with movement through said needle guide channel, and wherein said biopsy needle and cannula return to said curved configuration upon leaving said needle guide channel.

18. A system according to claim 1, wherein:
said needle guide channel defines a static curved path therethrough.

19. A system according to claim 1, wherein:
said needle guide channel has a moveable device for adjusting curvature of a path therethrough.

20. A system according to claim 1, wherein:
said needle guide body is selectively rotated about said longitudinal axis relative to said elongate housing and selectively moved along an axis parallel to said longitudinal axis relative to said elongate housing.

21. A system according to claim 1, wherein:
said needle guide body is rotatable about said longitudinal axis relative to said elongate housing such that said needle guide channel lies within one of said longitudinal scanning planes.

22. A system according to claim 1, wherein:
said needle guide channel includes an entrance and an exit, wherein said flexible biopsy needle and cannula set is operably received by said entrance and includes a portion that operably extends distally away from said exit into said body cavity.

23. A system according to claim 22, wherein:
said needle guide body is rotatable about said longitudinal axis relative to said elongate housing such that said portion of said biopsy needle and cannula set that operably extends distally away from said exit lies within a select one of said longitudinal scanning planes.

24. A system according to claim 23, wherein:
said portion of said biopsy needle and cannula set that operably extends distally away from said exit has a tip, and said needle guide body is moveable along the axis parallel to said longitudinal axis relative to said elongate housing such that said tip lies within a select one of said transverse scanning planes.

25. A system according to claim 1, further comprising:
first means for manual indexed adjustment of rotation of said needle guide body about said longitudinal axis relative to said elongate housing; and
second means for manual indexed movement of said needle guide body along the axis parallel to said longitudinal axis relative to said elongate housing.

26. A system according to claim 25, wherein:
said first means comprises a rotatable collar disposed adjacent a fixed collar.

27. A system according to claim 25, wherein:
said second means comprises a longitudinal slide and a longitudinal position controller.

28. A system according to claim 1, wherein:
said software system includes interface means for identifying a set of needle paths.

29. A system according to claim 28, wherein:
said interface means includes means for projecting a respective needle path onto an image of tissue adjacent the body cavity.

30. A system according to claim 29, wherein:
said respective needle path is shown as a line in the event that said image is parallel to said respective needle path, and said respective needle path is shown as a circle in the event that said image is pierced by said respective needle path.

31. A system according to claim 28, wherein:
said software system includes means for identifying and displaying coordinates for correlating position of said needle guide body to a respective needle path.

* * * * *